(12) United States Patent
Ye et al.

(10) Patent No.: US 8,642,347 B2
(45) Date of Patent: Feb. 4, 2014

(54) URINARY CA125 PEPTIDES AS BIOMARKERS OF OVARIAN CANCER

(75) Inventors: Bin Ye, Brookline, MA (US); Daniel Cramer, Chestnut Hill, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 341 days.

(21) Appl. No.: 12/865,508

(22) PCT Filed: Jan. 30, 2009

(86) PCT No.: PCT/US2009/000607
§ 371 (c)(1),
(2), (4) Date: Nov. 1, 2010

(87) PCT Pub. No.: WO2009/099561
PCT Pub. Date: Aug. 13, 2009

(65) Prior Publication Data
US 2011/0045508 A1 Feb. 24, 2011

Related U.S. Application Data

(60) Provisional application No. 61/006,783, filed on Jan. 31, 2008.

(51) Int. Cl.
*G01N 33/574* (2006.01)
*G01N 33/53* (2006.01)
*G01N 33/00* (2006.01)
*C12P 21/04* (2006.01)
*A61K 38/00* (2006.01)
*C07K 1/00* (2006.01)

(52) U.S. Cl.
USPC ............ 436/64; 435/7.1; 435/7.92; 435/69.6; 530/300; 530/326; 530/350

(58) Field of Classification Search
USPC ........ 435/7.1, 7.23, 7.92, 69.6; 530/300, 326, 530/350; 436/64
See application file for complete search history.

(56) References Cited

U.S. PATENT DOCUMENTS

| 4,921,790 | A | 5/1990 | O'Brien |
| 6,943,235 | B1 | 9/2005 | Afar et al. |
| 6,972,170 | B1 | 12/2005 | Cordon-Cardo et al. |
| 7,205,117 | B1 | 4/2007 | Robertson et al. |
| 7,244,827 | B2 | 7/2007 | Raitano et al. |
| 7,270,960 | B2 | 9/2007 | Hellstrom et al. |
| 7,288,383 | B2 | 10/2007 | Ye et al. |
| 7,294,704 | B2 | 11/2007 | Simon et al. |
| 7,402,403 | B1 | 7/2008 | Robertson et al. |
| 7,407,762 | B2 | 8/2008 | Auersperg et al. |
| 8,114,604 | B2 | 2/2012 | Robertson et al. |
| 2003/0078399 | A1 | 4/2003 | Lloyd et al. |
| 2003/0087250 | A1 | 5/2003 | Monahan et al. |
| 2003/0143667 | A1 | 7/2003 | O'Brien et al. |
| 2003/0211498 | A1 | 11/2003 | Morin et al. |
| 2005/0009120 | A1 | 1/2005 | Mok et al. |
| 2005/0059013 | A1 | 3/2005 | Chan et al. |
| 2005/0095592 | A1 | 5/2005 | Jazaeri et al. |
| 2006/0019256 | A1 | 1/2006 | Clarke et al. |
| 2006/0165676 | A1 | 7/2006 | Bergmann et al. |
| 2007/0026399 | A1 | 2/2007 | Auersperg et al. |
| 2007/0059712 | A1 | 3/2007 | Gish et al. |
| 2007/0172902 | A1 | 7/2007 | Zhang et al. |
| 2007/0178458 | A1 | 8/2007 | O'Brien et al. |
| 2007/0286865 | A1 | 12/2007 | Moore et al. |
| 2008/0081339 | A1 | 4/2008 | Liu et al. |
| 2008/0108084 | A1 | 5/2008 | Robertson et al. |
| 2008/0178308 | A1 | 7/2008 | Afar et al. |
| 2008/0253963 | A1 | 10/2008 | Morin et al. |
| 2008/0254048 | A1 | 10/2008 | Cheek et al. |
| 2008/0254481 | A1 | 10/2008 | Love et al. |
| 2008/0286199 | A1 | 11/2008 | Livingston et al. |
| 2009/0075305 | A1 | 3/2009 | Liu et al. |
| 2011/0028343 | A1 | 2/2011 | Alex et al. |
| 2012/0115749 | A1 | 5/2012 | Robertson et al. |
| 2012/0295814 | A1 | 11/2012 | Cramer et al. |
| 2013/0090251 | A1 | 4/2013 | Robertson et al. |

FOREIGN PATENT DOCUMENTS

| WO | WO 00/26666 A2 | 5/2000 |
| WO | WO 03/072752 A2 | 9/2003 |
| WO | WO 2005/024055 A1 | 3/2005 |
| WO | WO 2006/119155 A2 | 11/2006 |
| WO | WO 2008/060363 A2 | 5/2008 |
| WO | WO 2009/145815 A2 | 12/2009 |
| WO | WO 2011/085165 A2 | 7/2011 |
| WO | WO 2012/125805 A2 | 9/2012 |

OTHER PUBLICATIONS

Moore et al. (Gynecol Oncol. Feb. 2008; 108(2): 402-8. Epub Dec. 3, 2007).*
Timms et al. (Cancer Genomics & Proteomics, 2011, 8: 289-306).*
Halila et al. (Br J Cancer. Aug. 1987; 56(2): 153-6).*
Written Opinion of the International Searching Authority for PCT/US2009/000607 filed Jan. 30, 2009.
International Preliminary Report on Patentability for PCT/US2009/000607 filed Jan. 30, 2009.
GenBank Accession No. AAL65133; ovarian cancer related tumor marker CA125 [Homo sapiens], Oct. 29, 2002.
Badgwell, et al., "Urinary mesothelin provides greater sensitivity for early stage ovarian cancer than serum mesothelin, urinary hCG free beta subunit and urinary hCG beta core fragment," *Gynecologic Oncology* 106:490-497 (2007).
Chambers, et al., "Ovarian Cancer Biomarkers in Urine," *Clin. Cancer Res.* 12(2):323-327 (Jan. 2006).

(Continued)

*Primary Examiner* — Stephen Rawlings
*Assistant Examiner* — Yan Xiao
(74) *Attorney, Agent, or Firm* — Law Office of: Michael A. Sanzo, LLC

(57) ABSTRACT

The present invention is directed to diagnostic methods based upon the detection of peptides derived from the degradation of CA125. In particular, it is concerned with assays of urine samples collected from women for the purpose of determining whether they are at increased risk for having ovarian cancer, have decreased their risk as the result of clinical or non-clinical procedures, to monitor the efficacy of a treatment method, or to determine whether cancer has recurred or advanced.

20 Claims, No Drawings

(56) References Cited

OTHER PUBLICATIONS

Drapkin, et al., "Human Epididymis Protein 4 (HE4) Is a Secreted Glycoprotein that Is Overexpressed by Serous and Endometrioid Ovarian Carcinomas," *Cancer Res.* 65(6):2162-2169 (Mar. 2005).
Gagnon, et al. "Discovery and application of protein biomarkers for ovarian cancer," *Curr. Opin. Obstet. Gynecol.* 20:9-13 (2008).
Gagnon, et al.. "Use of a Combination of Approaches to Identify and Validate Relevant Tumor-Associated Antigens and Their Corresponding Autoantibodies in Ovarian Cancer Patients," *Clin. Cancer Res.* 14(3):764-771 (2008).
Geho, et al., "Nanoparticles: potential biomarker harvesters," *Curr. Opin. Chem Biol.* 10(1):56-61 (2006).
Georganopoulou, et al., "Nanoparticle-based detection in cerebral spinal fluid of a soluble pathogenic biomarker for Alzheimer's disease," *PNAS* 102(7):2273-2276 (Feb. 2005).
Hellström, et al., "The HE4 (WFDC2) Protein Is a Biomarker for Ovarian Carcinoma," *Cancer Res.* 63:3695-3700 (Jul. 2003).
Hellström, et al., "SMRP and HE4 as Biomarkers for Ovarian Carcinoma When Used Alone and in Combination with CA125 and/or Each Other," *Adv. Exp. Med. Biol.* 622:15-21 (2008).
Jain, "Nanotechnology in clinical laboratory diagnostics," *Clinica Chimica Acta* 358:37-54 (2005).
Lowe, et al., "Effects of Personal Characteristics on Serum CA125, Mesothelin, and HE4 Levels in Healthy Postmenopausal Women at High-Risk for Ovarian Cancer," *Cancer Epidemiol Biomarkers Prev* 17(9):2480-2487 (Sep. 2008).
Moore, et al., "The use of multiple novel tumor biomarkers for the detection of ovarian carcinoma in patients with a pelvic mass," *Gynecologic Oncology* 108:402-408 (2008).
Moore, et al., "A novel multiple marker bioassay utilizing HE4 and CA125 for the prediction of ovarian cancer in patients with a pelvic mass," *Gynecologic Oncology* 112:40-46 (2009).
O'Brien, et al., "The CA 125 Gene: An Extracellular Superstructure Dominated by Repeat Sequences," *Tumor Biol* 22:348-366 (2001).
Pisitkun, et al., "Discovery of Urinary Biomarkers," *Mol. Cell. Proteomics* 5:1760-1771 (2006).
Roy, et al., "ADAM 12 Cleaves Extracellular Matrix Proteins and Correlates with Cancer Status and Stage," *J. Biol. Chem.* 279(49):51323-51330 (2004).
Schaner, et al., "Gene Expression Patterns in Ovarian Carcinomas," *Mol. Biol. Cell* 14:4376-4386 (Nov. 2003).
Scholler, et al., "Use of Yeast-Secreted In vivo Biotinylated Recombinant Antibodies (Biobodies) in Bead-Based ELISA," *Clin. Cancer Res.* 14(9):2647-2655 (May 2008).
Scholler, et al., "Bead-Based ELISA for Validation of Ovarian Cancer Early Detection Markers," *Clin. Cancer Res.* 12(7):2117-2124 (Apr. 2006).
Schummer, et al., "Comparative hybridization of an array of 21 500 ovarian cDNAs for the discovery of genes overexpressed in ovarian carcinomas," *Gene* 238:375-385 (1999).
Shenoy, et al., "Surface functionalization of gold nanoparticles using hetero-bifunctional poly(ethylene glycol) spacer for intracellular tracking and delivery," *Int. J. Nanomedicine* 1(1):51-57 (2006).
Tantipaiboonwong, et al., "Different techniques for urinary protein analysis of normal and lung cancer patients," *Proteomics* 5:1140-1149 (2005).
Tay, et al., "Correlation of Serum, Urinary and Salivary CA 125 Levels in Patients with Adnexal Masses," *Ann. Acad. Med. Singapore* 23(3):311-314 (1994).
Terry, et al., "Blood and urine markers for ovarian cancer: A comprehensive review," *Disease Markers* 20:53-70 (2004).
Wang, et al., "Gold Nanoparticle-Assisted Protein Enrichment and Electroelution for Biological Samples Containing Low Protein Concentration—A Prelude of Gel Electrophoresis," *J. Proteome Res.* 5(6):1488-1492 (2006).
Ye, et al., "Recent technical strategies to identify diagnostic biomarkers for ovarian cancer," *Expert Rev. Proteomics* 4(1):121-131 (2007).
Ye, et al., "Proteomic-Based Discovery and Characterization of Glycosylated Eosinophil-Derived Neurotoxin and COOH-Terminal Osteopontin Fragments for Ovarian Cancer in Urine," *Clin. Cancer Res.* 12(2):432-441 (Jan. 2006).
Ye, et al., "Haptoglobin-α Subunit As Potential Serum Biomarker in Ovarian Cancer: Identification and Characterization Using Proteomic Profiling and Mass Spectrometry," *Clin. Cancer Res.* 9:2904-2911 (Aug. 2003).
Yin, et al., "Molecular Cloning of the CA125 Ovarian Cancer Antigen," *J. Biol. Chem.* 276(29):27371-27375 (Jul. 2001).
Agaylan, et al., "A Highly Sensitive Particle Agglutination Assay for the Detection of P53 Autoantibodies in Patients With Lung Cancer," *Cancer* 110(11):2502-2506 (2007).
Anderson, et al. "The Human Plasma Proteome: History, Character, and Diagnostic Prospects," *Mol. Cell. Proteomics* 1(11):845-867 (2002).
Angelopoulou, et al., "Autoantibodies against the p53 tumor suppressor gene product quantified in cancer patient serum with time-resolved immunofluorometry," *Cancer J.* 6(6):315-321 (Nov.-Dec. 1993).
Anim, et al., "Characterisation of inflammatory cells in benign prostatic hyperplasia," *Acta. Histochem.* 100(4):439-449 (1998).
Ashton, et al., "The Association of the COMT V158M Polymorphism with Endometrial/Ovarian Cancer in HNPCC Families Adhering to the Amsterdam Criteria," *Hereditary Cancer in Clinical Practice* 4(2):94-102 (2006).
Bartling, et al., "Comparative application of antibody and gene array for expression profiling in human squamous cell lung carcinoma," *Lung Cancer* 49:145-154 (2005).
Boccarelli, et al., "Differential processing of antitumor-active and antitumor-inactive trans platinum compounds by SKOV-3 ovarian cancer cells," *Biochem. Pharm.* 72(3):280-292 (Jul. 2006).
Bouwman, et al., "Microarrays of tumor cell derived proteins uncover a distinct pattern of prostate cancer serum immunoreactivity," *Proteomics* 3:2200-2207 (2003).
Bradford, et al., "Cancer immunomics: Using autoantibody signatures in the early detection of prostate cancer," *Urologic Oncol. Sem. Orig. Invest.* 24:237-242 (2006).
Brawer, et al., "Prostate-Specific Antigen: Current Status," *CA Cancer J. Clin.* 49(5):264-281 (1999).
Di Silverio, et al., "Distribution of Inflammation, Pre-Malignant Lesions, Incidental Carcinoma in Histologically Confirmed Benign Prostatic Hyperplasia: A Retrospective Analysis," *Eur. Urol.* 43(2):164-175 (2003).
Ehrlich, et al., "The reverse capture autoantibody microarray: a native antigen-based platform for autoantibody profiling," *Nat. Protocols* 1(1):452-460 (2006).
Fong, et al., "Natural history and clinical predictors of clinical progression in benign prostatic hyperplasia," *Curr. Opin. Urol.* 15:35-38 (2005).
Fossa, et al., "Serological cloning of cancer/testis antigens expressed in prostate cancer using cDNA phage surface display," *Cancer Immunol. Immunother.* 53:431-438 (2004).
Koziol, et al., "Recursive Partitioning as an Approach to Selection of Immune Markers for Tumor Diagnosis," *Clinical Cancer Research* 9:5120-5126 (Nov. 2003).
Lang, et al., "p53 autoantibodies in patients with urological tumors," *Br. J. Urol.* 82(5):721-726 (1998).
Lee, et al., "Immunomic analysis of human sarcoma," *Proc. Natl. Acad. Sci. USA* 100(5):2651-2656 (Mar. 2003).
Liang, et al., "Anti-5α-Reductase Autoantibodies in the Serum of Patients with Prostatic Cancer," *J. Clin. Endocrinol Metab.* 71(6):1666-1668 (1990).
Liu, et al., "Proteomics approaches to urologic diseases," *Expert Rev. Proteomics* 3(3):283-296 (2006).
Luo, et al., "Human Prostate Cancer and Benign Prostatic Hyperplasia: Molecular Dissection by Gene Expression Profiling," *Cancer Res.* 61(12):4683-4688 (Jun. 2001).
Luo, et al., "Gene Expression Signature of Benign Prostatic Hyperplasia Revealed by cDNA Microarray Analysis," *Prostate* 51(3):189-200 (2002).
Mahapokai, et al., "Immune response in hormonally-induced prostatic hyperplasia in the dog," *Vet. Immunol. Immunopathol.* 78(3-4):297-303 (2001).
Maxwell, et al., "Novel *PEX1* Coding Mutations and 5' UTR Regulatory Polymorphisms," *Human Mutation* 26(3):279; pp. 1-8 (Sep. 2005).
McAndrew, et al., "Development of a panel of biomarkers for the diagnosis of prostate cancer," AACR Meeting Sep. 27-30, 2010, Denver Colorado, Poster Session A.

(56) References Cited

OTHER PUBLICATIONS

McConnell, et al., "The Long-Term Effect of Doxazosin, Finasteride, and Combination Therapy on the Clinical Progression of Benign Prostatic Hyperplasia," *N. Engl. J. Med.* 349(25):2387-2398 (Dec. 2003).
Miller, et al., "Antibody microarray profiling of human prostate cancer sera: Antibody screening and identification of potential biomarkers," *Proteomics* 3:56-63 (2003).
Mintz, et al., "Fingerprinting the circulating repertoire of antibodies from cancer patients," *Nat. Biotechnol.* 21:57-63 (Jan. 2003).
Nickel, et al., "Asymptomatic inflammation and/or infection in benign prostatic hyperplasia," *B. J. Urol.* 84(9):976-981 (1999).
Nilsson, et al., "Autoantibodies to Prostasomes as New Markers for Prostate Cancer," *Ups. J. Med. Sci.* 106(1): 43-49 (2001).
Peiro, et al., "CAS (Cellular Apoptosis Susceptability) Gene Expression in Ovarian Carcinoma," *American Journal of Clinical Pathology* 118(6):922-929 (2002).
Prakash, et al., Symptomatic and asymptomatic benign prostatic hyperplasia: molecular differentiation by using microarrays, *Proc. Nat'l. Acad. Sci. USA* 99(11):7598-7603 (May 2002).
Qin, et al., "Development of a reverse capture autoantibody microarray for studies of antigen-autoantibody profiling," *Proteomics* 6:3199-3209 (2006).
Qiu, et al., "Development of Natural Protein Microarrays for Diagnosing Cancer Based on an Antibody Response to Tumor Antigens," *Proteome Res.* 3(2): 261-267 (2004).
Roessler, et al., "Identification of PSME3 as a Novel Serum Tumor Marker for Colorectal Cancer by Combining Two-dimensional Polyacrylamide Gel Electrophoresis with a Strictly Mass Spectrometry-based Approach for Data Analysis," *Mol. Cell. Prot.* 5(11):2092-2101 (2006).
Roessler, et al., "Identification of Nicotinamide *N*-Methyltransferase as a Novel Serum Tumor Marker for Colorectal Cancer," *Clin. Can. Res.* 11(18):6550-6557 (Sep. 2005).
Segawa, et al., "Measurement and evaluation of serum anti-p53 antibody levels in patients with lung cancer as its initial presentation: a prospective study," *Br J Cancer* 78(5):667-72 (1998).
Song, et al., "Annexin XI Is Associated with Cisplatin Resistance and Related to Tumor Recurrence in Ovarian Cancer Patients," *Clin. Cancer Res.* 13(22):6842-6849 (Nov. 2007).
Soussi, et al., "p53 Antibodies in the Sera of Patients with Various Types of Cancer: A Review," *Cancer Res.* 60:1777-1788 (Apr. 2000).
Stoll, et al., "Microarray technology: an increasing variety of screening tools for proteomic research," *Drug Discovery Today: Targets* 3(1):24-31 (Feb. 2004); XP002569004.
Tan, et al., "Autoantibodies as reporters identifying aberrant cellular mechanisms in tumorigenesis," *J.Clin. Invest.* 108:1411-1415 (Nov. 2001).
Tang, et al., "Autoantibody profiling to identify biomarkers of key pathogenic pathways in mucinous ovarian cancer," *European Journal of Cancer* 46:170-179 (2010).
Tramontano, et al., "Conformation and Glycosylation of a Megalin Fragment Correlate with Nephritogenicity in Heymann Nephritis," *J. Immunol.* 172:2367-2373 (2004).
Turhan, et al., "Adenosquamous Carcinoma of the Prostate," *Int. Urol. Nephrol.* 31(1):89-93 (1999).
UniProtKB/Swiss-Prot database entry 043933 for PEX-1, sequence last modified Aug. 10, 2010.
Wanders, "Metabolic and Molecular Basis of Peroxisomal Disorders: A Review," *Am. J. Med. Genet.* 126A:355-375 (2004).
Wang, et al., "Autoantibody Signatures in Prostate Cancer," *N. Engl. J. Med.* 353(12):1224-1235 (Sep. 2005).
Wiener, et al. "Activated Src protein tyrosine kinase is overexpressed in late-stage human ovarian cancers," *Gynecologic Oncology* 88(1):73-79 (Jan. 2003).
Xu, et al., "Screening of the metastasis-associated genes by gene chip in high metastatic human ovarian cancer cell lines," *Journal of Genetics and Genomics* 34(7):581-590 (Jul. 2007).

Yan, et al., "Rapid and sensitive immunomagmetic-electrochemiluminescent detection of p53 antibodies in human serum," *J Immunol Methods* 288:47-54 (2004).
Yazan, et al., "Proteomic Analysis of Waldenstrom Macroglobulinemia (WM) Using Nanoscale Protein Microarray Techniques," *Blood* 106:Abstract 504 (2005).
Zha, et al., "Peroxisomal Branched Chain Fatty Acid β-Oxidation Pathway Is Upregulated in Prostate Cancer," *The Prostate* 63:316-323 (2005).
Zhang, et al., "Enhancement of Antibody Detection in Cancer Using Panel of Recombinant Tumor-associated Antigens," *Cancer Epidemiology, Biomarkers and Prevention* 12(2):136-143 (Feb. 2003).
Zhang, et al., "Tumor-associated antigen arrays to enhance antibody detection for cancer diagnosis," *Cancer Detect. Prev.* 28:114-118 (2004).
Zhou, et al., "Serological Cloning of PARIS-I: A New TBC Domain-Containing, Immunogenic Tumor Antigen from a Prostate Cancer Cell Line," *Biochem. Biophys. Res. Commun.* 290:830-838 (2002).
Zolg, et al., "How Industry Is Approaching the Search for New Diagnostic Markers and Biomarkers," *Mol. Cell. Prot.* 3:345-354 (2004).
Crammer, et al., "CA125 Immune Complexes in Ovarian Cancer Patients with Low CA125 Concentrations," *Clin. Chem.* 56(12):1889-1892 (2010).
Crammer, et al., "Conditions Associated with Antibodies Against the Tumor-Associated Antigen MUC1 and Their Relationship to Risk for Ovarian Cancer," *Cancer Epidemiology, Biomarkers & Prevention* 14:1125-1131 (2005).
Ehrlich, et al., "A native antigen "reverse capture" microarray platform for autoantibody profiling of prostate cancer sera," *Proteomics Clin. Appl.* 1(5):476-485 (2007).
Finn, "Immune Response as a Biomarker for Cancer Detection and a Lot More," *N. Engl. J. Med.* 353(12):1288-1290 (Sep. 2005).
Kalia, et al., "General Method for Site-Specific Protein Immobilization by Staudinger Ligation," *Bioconjugate Chem.* 18(4):1064-1069 (2007).
Rusmini, et al., "Protein Immobilization Strategies for Protein Biochips," *Biomacromolecules* 8:1775-1789 (2007).
Tang, et al., "Autoantibody biomarker profiling for mucinous ovarian cancers," Poster 99th AACR Annual Meeting, Apr. 12-16, 2008; Abstract #4450.
Tockman, et al., "Considerations in Bringing a Cancer Biomarker to Clinical Application," *Cancer Res.* 52:2711s-2718s (May 1992).
Wilson, et al., "Functional protein microarrays," *Curr. Opin. Chem. Biol.* 6(1):81-85 (2001).
Zhu, et al., "Protein chip technology," *Curr. Opin. Chem. Biol.* 7(1):55-63 (2003).
U.S. Appl. No. 13/520,665, filed Jul. 5, 2012, Cramer.
O'Rourke, et al., "Autoantibody signatures as biomarkers to distinguish prostate cancer from benign prostatic hyperplasia in patients with increased serum prostate specific antigen," *Clinica Chimica Acta* 413:561-567 (2012).
Rodriguez, et al., "Casein kinase I epsilon interacts with mitochondrial proteins for the growth and survival of human ovarian cancer cells," *EMBO Mol Med.* 4:1-12 (2012).
Taylor, et al., "Patient-derived tumor-reactive antibodies as diagnostic markers for ovarian cancer," *Gynecologic Oncology* 115:112-120 (2009).
Kim, et al., "Identification of Epithelial Cell Adhesion Molecule Autoantibody in Patients with Ovarian Cancer," *Clin. Cancer Res.* 9:4782-4791 (2003).
Fu, et al., "Flow-Through Multianalyte Chemiluminescent Immunosensing System with Designed Substrate Zone-Resolved Technique for Sequential Detection of Tumor Markers," *Anal. Chem.* 78(19):6999-7005 (Oct. 2006).
International Search Report for PCT/US2009/000607, Sep. 2009.
"BD Clontech Antibody (Ab) Microarray 500" In: "Product overview" Clontech Laboratories Inc., Mountain View CA 94043 USA; XP002569005 (Jul. 2004).
Ries, el al., SEER Cancer Stat. Rev. 1973-1995 National Cancer Institute, Bethesda, MD; Tables XX-1 through XX-9; Figures XX-1, XX-2 and XX-3 (1998).

\* cited by examiner

SEQUENCE LISTING

```
<160> NUMBER OF SEQ ID NOS: 3

<210> SEQ ID NO 1
<211> LENGTH: 18
<212> TYPE: PRT
<213> ORGANISM: Homo sapiens

<400> SEQUENCE: 1

Asp Ser Leu Tyr Val Asn Gly Phe Thr His Gln Ser Ser Met Thr Thr
1               5                   10                  15

Thr Arg

<210> SEQ ID NO 2
<211> LENGTH: 15
<212> TYPE: PRT
<213> ORGANISM: Homo sapiens

<400> SEQUENCE: 2

Ser Ser Gly Val Thr Phe Ser Arg Pro Asp Pro Thr Ser Lys Lys
1               5                   10                  15

<210> SEQ ID NO 3
<211> LENGTH: 15
<212> TYPE: PRT
<213> ORGANISM: Homo sapiens

<400> SEQUENCE: 3

His Pro Phe Ser Ser Pro Glu Pro Asp Ser Ala Gly His Thr Lys
1               5                   10                  15
```

URINARY CA125 PEPTIDES AS BIOMARKERS OF OVARIAN CANCER

CROSS REFERENCE TO RELATED APPLICATIONS

The present application is US national stage of international application PCT/US2009/000607, which had an international filing date of Jan. 30, 2009, and claims the benefit of U.S. provisional application 61/006,783 filed on Jan. 31, 2008 the contents of which is hereby incorporated by reference in its entirety. The international application was published in English under PCT Article 21(2) on Aug 13, 2009.

STATEMENT OF GOVERNMENT FUNDING

The United States Government has a paid-up license in this invention and the right in limited circumstances to require the patent owner to license others at reasonable terms as provided for by the terms of NIH Grant No. R21CA111949-01 awarded by the Department of Health and Human Services.

FIELD OF THE INVENTION

The present invention is in the field of tumor cell markers and is particularly concerned with methods of detecting ovarian cancer by assaying urine samples for CA125 peptides. Any method for determining CA125 peptide levels may be used, including mass spectroscopy assays, radioimmunoassays and ELISA assays.

BACKGROUND OF THE INVENTION

Ovarian cancer is the fifth leading cause of death from cancer in US women. In most instances, a diagnosis is not made until the cancer is in an advanced state, at a time when the five year survival rate of patients is only about 28% (Ries, et al., *SEERC Cancer Stat. Rev.* 1973-1995 (1998)). In contrast, the five year survival rate for women diagnosed with localized disease is about 95%. These statistics provide an incentive to search for new diagnostic tests for this disease, especially those that can be used in screening patients and which may detect cancer at an early stage.

Over the last several years, efforts at the discovery of biomarkers for ovarian cancer have focused primarily on serum and plasma. Relatively little attention has been paid to urinary biomarkers despite advantages that urine-based tests have in terms of non-invasiveness, convenience and cost. Although urine assays have been traditionally used for urinary tract diseases, more recent studies have indicated that these assays are also valuable in the detection of other diseases as well (Pisitkun, et al., *Mol. Cell. Proteomics* 5:1760-1771 (2006)) including lung cancer (Tantipaiboonwong, et al., *Proteomics* 5:1140-1149 (2005) and breast cancer (Roy, et al., *J. Biol. Chem.* 279:51323-51330 (2004)). Assays of glycosylated forms of eosinophil-derived neurotoxin and COOH-terminal peptides of osteopontin in urine have been found to be associated with ovarian cancer malignancy (Ye, et al., *Clin. Cancer Res.* 12:432-441 (2006); Chambers, et al., *Clin. Cancer Res.* 12:323-327 (2006); U.S. Pat. No. 7,288,383; US 2005009120).

The most commonly used plasma assay for detecting ovarian cancer is for the CA125 biomarker. However this test is of limited sensitivity and is poor at detecting ovarian cancer in its early stages, when the disease is most treatable. These limitations may be, at least in part, due to the complicated structure of the CA125 protein and interference from high levels of other plasma proteins. An assay of urine for peptides generated during the breakdown of CA125 may avoid these problems and would be well suited to the widespread screening of patients.

SUMMARY OF THE INVENTION

Human CA125 is a heavily glycosylated protein of 1890 amino acids that has been completely sequenced (Yin, et al., *J. Biol. Chem.* 276:27371-27375 (2001), incorporated herein by reference in its entirety) and which is used as a serum marker for ovarian cancer. The present invention is based upon the discovery that peptides generated during the degradation of CA125 are present in the urine of patients with ovarian cancer but are essentially absent in urine samples from normal, healthy women or women with benign ovarian tumors. There is a correlation between serum levels of CA125 and urine levels of Ca125 peptides suggesting that assays of the urine peptides may be used in a similar manner to serum assays. However, a urine based assay should be easier to perform, is noninvasive and is amenable to use in kits for testing at home. In addition, urine has far fewer proteins likely to interfere with assays than serum and may therefore be more sensitive and reliable.

In its first aspect, the invention is directed to a method of diagnostically evaluating a woman for the presence of ovarian cancer. This is accomplished by obtaining a test urine sample from the woman and then assaying it to determine the amount or concentration of at least one CA125 peptide present. The term "CA125 peptide" refers to degradation products of the 1890 amino acid human CA125 found in serum. A CA125 peptide will always have an amino acid sequence matching a segment of the CA125 protein but will be shorter in length. Peptides may be 10-500 amino acids in length but are preferably 10-60 amino acids long and more preferably 10-20 amino acids long.

Results obtained from the assay of the test urine sample are compared with results obtained from similar assays performed on one or more control samples and it is concluded that the woman from which the urine sample was obtained is positive for ovarian cancer if the concentration or amount of CA125 peptide in the test sample is higher than the concentration or amount found in the control sample. Methods for selecting appropriate controls are well known in the art. For example, controls may be urine samples obtained from women believed to be free from malignant disease or they may simply be urine samples obtained from the general population of women. It will be understood that once a normal range for the peptide is established, test sample values may be simply compared to the normal range without the need to run new control samples with each assay. Although no assay short of a full biopsy is 100 percent reliable in predicting cancer, the finding that a sample is "positive" for ovarian cancer due to elevated urine CA125 peptide levels means that the woman from which the sample is derived is at an increased risk of having the disease and is in need of further evaluation.

In general, there should be no/or less detectable CA125 peptides in the urine of healthy women or of women with benign tumors. At a minimum, the CA125 peptide will be 3 times higher in women with ovarian cancer. Any means for detecting and quantitating the presence of the urine peptides is compatible with the invention. Examples of assays that can be used include: radioimmunoassays (RIAs), Enzyme Linked Immunosorbent Assays (ELISAs), chromatographic assays and mass spectroscopic assays. Specific peptides may be separated from one another using standard techniques and identified as being a CA125 degradation product based upon their sequence or based upon their reactivity with CA125 specific antibodies. Monoclonal antibodies recognizing only specific peptides may also be used. If necessary CA125 peptides may be deglycosylated prior to assay using standard techniques.

The urine assays described above for the detection of CA125 may be combined with other tests for ovarian cancer to gain further information on the likelihood of this disease being present. For example, the assay of urine for CA125 peptides may be used in conjunction with standard assays for serum or plasma levels of CA125 protein. The most preferred peptides for analysis in the urine assays are:

| a) | DSLYVNGFTHQSSMTTTR; | (SEQ ID NO: 1) |
|---|---|---|
| b) and | SSGVTFSRPDPTSKK; | (SEQ ID NO: 2) |
| c) | HPFSSPEPDSAGHTK. | (SEQ ID NO: 3) |

All sequences shown are from the N to C terminus and use standard one letter abbreviations for amino acids.

It will be understood that the peptides being assayed may be glycosylated to varying degrees, due to glycosylation of the intact CA125 from which they are derived. If present, glycosylation would typically be found at the hydroxy oxygen of serine or threonine or at the amide nitrogen of asparagine. Glycosylation may be removed or left in place depending upon the type of assay used.

Modifications may also be deliberately made in synthetic peptides, for example to increase antigenicity. For example, prior to the generation of antibodies one or more amino acid residues may be conservatively substituted with a functionally similar residue. Examples of conservative substitutions include: the substitution of one hydrophobic aliphatic residue, such as isoleucine, valine, leucine or alanine, for another; the substitution of one hydrophobic aromatic residue, such as phenylalanine, tryptophan and tyrosine, for another; the substitution of one polar (hydrophilic) residue for another, such as between glutamine and asparagine, or between cysteine, methionine, threonine and serine; the substitution of one basic residue such as lysine, arginine or histidine for another, or the substitution of one acidic residue, such as aspartic acid or glutamic acid for another.

Peptides may also undergo standard chemical derivatization procedures if desired. For example, free amino groups may be derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are peptides which are modified to contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine.

The assay methods described above may be used on women that have not been previously diagnosed as having ovarian cancer (e.g., in a screening assay) to help evaluate whether cancer is present. They may also be used for women that have been diagnosed as having ovarian cancer to determine the efficacy of treatment, or to determine if the cancer has recurred or advanced.

In another aspect, the invention is directed to a method of diagnostically evaluating a woman for ovarian cancer by: obtaining a test urine sample; performing an immunoassay on the test urine sample to determine the amount or concentration of CA125 antigenic activity present; comparing the results obtained with results from an assay of one or more control urine samples from women without ovarian cancer or from the general population; and concluding that the woman tested is positive for ovarian cancer if the amount or concentration of CA125 antigenic activity is higher in the test urine sample than in the control urine sample. The main difference between this assay and the assays discussed above is that, in the present case, a composite antigenic activity (i.e., activity from all peptides recognized by the antibody) is determined rather than the level of a specific peptide. Depending on the specificity of the antibodies used in the immunoassays, antigenic activity may reflect all or part of the total CA125 peptides present. In general, immunoassays utilizing a polyclonal antibody against CA125 are preferred. As discussed above, this assay may be used on patients not yet diagnosed as having ovarian cancer to test for its presence. Alternatively it may be used in patients known to have ovarian cancer to evaluate whether the disease has recurred or advanced. It may also be used in conjunction with other diagnostic assays such as serum or plasma assays for CA125.

As suggested above, the peptides that have been determined to be biomarkers for ovarian cancers are: DSLYVNGFTHQSSMTTTR (SEQ ID NO:1); SSGVTFSRPDPTSKK (SEQ ID NO:2); and HPFSSPEPDSAGHTK (SEQ ID NO:3). Antibodies reacting with these peptides may be made for use in the urine assays for ovarian cancer. This can be accomplished by administering the CA125 peptide to an immunocompetent animal, i.e., an animal capable of generating antibodies such as a rabbit, goat or horse. The peptides must be given in an amount sufficient to induce antibody production and may be recovered from animals using methods that are well known in the art. Alternatively monoclonal antibodies may be made by isolating splenocytes from the animals given peptide, fusing these to melanocytes and then producing antibodies using hybridoma technology.

The biomarker CA125 peptides described above may be sold as part of a kit for performing diagnostic assays for ovarian cancer. In addition to one or more of the peptides, the kit should include other components needed to carry out assays in people. In general, this means that the kit will include at least one antibody (preferably a monoclonal antibody) that reacts specifically with one or more of the CA125 peptides present, i.e., that reacts at least 100 times more strongly with the CA125 peptide(s) than with other peptides. The antibody may optionally be linked to an enzyme that can be used for detecting peptide in an ELISA assay or it can be bound to a radioisotope for use in a radioimmunoassay. The kit may also include other components such as buffers or control samples that can be used in assays.

DETAILED DESCRIPTION OF THE INVENTION

The discovery of a correlation between the concentration of CA125 peptides in urine and ovarian cancer is consistent with serum assays on intact CA125 that are presently used clinically. The complete amino acid and nucleotide sequence of human CA125 is known (see Yin, et al., *J. Biol. Chem.* 276:27371-27375 (2001)) and assays that have been used for detecting intact CA125 in serum or plasma samples can be used for the detection of peptide in urine (see e.g., the Examples section herein). Normally such assays would be performed after the fractionation of the peptides by techniques such as electrophoresis or chromatography. Alternatively, non-immunological methods such as mass spectroscopy may be used or peptides may be identified without fractionation if monoclonal antibodies that are highly specific for the peptides are used.

Any type of quantitative assay is compatible with the invention including immunoassay procedures performed using, for example, commercially available monoclonal or polyclonal antibodies for CA125. Alternatively, CA125 peptides may be synthesized and immunoassays may be developed based upon the production of new antibodies that bind specifically to the peptides.

Antibodies that bind specifically to a CA125 peptide are defined for the purpose of the present invention as those that have at least a 100 fold greater affinity for the peptide than for any other peptide found in urine. The process for producing such antibodies involves injecting the peptide itself into an appropriate animal. Methods for making and detecting antibodies are well known to those of skill in the art as evidenced by standard reference works such as: Harlow, et al., *Antibodies, A Laboratory Manual*, Cold Spring Harbor Laboratory, NY (1988); Klein, *Immunology: The Science of Self-Nonself Discrimination* (1982); Kennett, et al., *Monoclonal Antibodies and Hybridomas: A New Dimension in Biological Analyses* (1980); and Campbell, "Monoclonal Antibody Technology," in: *Laboratory Techniques in Biochemistry and Molecular Biology* (1984).

"Antibody" as used herein is meant to include intact molecules as well as fragments which retain the ability to bind antigen (e.g., Fab and F(ab') fragments). These fragments are typically produced by proteolytically cleaving intact antibodies using enzymes such as a papain (to produce Fab fragments) or pepsin (to produce F(ab')$_2$ fragments). The term "antibody" also refers to both monoclonal antibodies and polyclonal antibodies. Polyclonal antibodies are derived from the sera of animals immunized with the antigen. Monoclonal antibodies can be prepared using hybridoma technology (Kohler, et al., *Nature* 256:495 (1975)). In general, this technology involves immunizing an animal, usually a mouse, with the CA125 peptide. The splenocytes of the immunized animals are extracted and fused with suitable myeloma cells, e.g., SP$_2$O cells. After fusion, the resulting hybridoma cells are selectively maintained in a culture medium and then cloned by limiting dilution (Wands, et al., *Gastroenterology* 80:225-232 (1981)). The cells obtained through such selection are then assayed to identify clones which secrete antibodies capable of binding to CA125 peptide.

The antibodies or fragments of antibodies described above may be used to detect the presence of the CA125 peptide in any of a variety of immunoassays. For example, antibodies may be used in radioimmunoassays or immunometric assays, also known as "two-site" or "sandwich assays" (see Chard, "Introduction to Radioimmune Assay and Related Techniques," in: *Laboratory Techniques in Biochemistry and Molecular Biology*, North Holland Publishing Co., N.Y. (1978)). In a typical immunometric assay, a quantity of unlabelled antibody is bound to a solid support that is insoluble in the fluid being tested. After the initial binding of antigen to immobilized antibody, a quantity of detectably labeled second antibody (which may or may not be the same as the first) is added to permit the detection and/or quantitation of bound antigen (see e.g., *Radioimmune Assay Method*, Kirkham, et al., ed., pp. 199-206, E&S Livingston, Edinburgh (1970)). Many variations of these types of assays are known in the art and may be employed for the detection of CA125 peptide.

If desired, antibodies to a CA125 peptide may also be used in the purification of the peptide (see generally, Dean, et al., *Affinity Chromatography, A Practical Approach*, IRL Press (1986)). Typically, antibody is immobilized on a chromatographic matrix such as Sepharose 4B™. The matrix is then packed into a column and the preparation containing the CA125 peptide is passed through under conditions that promote binding, e.g., under conditions of low salt. The column is then washed and bound peptide is eluted using a buffer that promotes dissociation of antibody, e.g., a buffer having an altered pH or salt concentration. The eluted peptide may be transferred into a buffer of choice and either stored or assayed directly.

EXAMPLES

The purpose of this study was to identify urinary peptides and metabolites derived from the cancer biomarker CA125 that may be used as non-invasive biomarkers for ovarian cancer and associated conditions such as benign tumors, and in the detection of early cancer metastasis.

Materials and Methods

Urine specimens pre-operatively collected from ovarian cancer patients and normal healthy women were used in this study for protein and peptide identification and measurements. Mass spectrometry was used to identify urine CA125 peptide sequences based upon comparison with a standard CA125 control after trypsin digestion. Monoclonal antibody from a commercially available source was used for Western blot analysis, and dot blot semi-quantification. Commercial ELISA assays and standardized clinical CA125 assays (radioimmune arrays) were performed on the same set of 20 normal, 20 benign and 20 ovarian cancer patients.

Results

We found that urine CA125 peptides were detectable in Western blots, dot blots, mass spectrometry profiles and standard CA125 immune assays. Three peptides were identified that were present in samples from cancer patients but either entirely absent from, or greatly reduced in, samples from normal women. Western blots performed using monoclonal antibody revealed a CA125 fragment of about 25 kDa. Using mass spectrometry, two polypeptides (1593, 2045, m/z) were identified in urine specimens of ovarian cancer patients which appeared to be identical to standard CA125 peptides. Protein sequence analysis, revealed that the peptides had the following amino acid sequences: DSLYVNGFTHQSSMTTTR (SEQ ID NO:1); SSGVTFSRPDPTSKK (SEQ ID NO:2); and HPFSSPEPDSAGHTK (SEQ ID NO:3).

Using a standard CA125 assay on urine specimens collected from age-matched normal healthy women and pre-operative patients with ovarian benign and serous type of ovarian cancer disease, we found that there is a significant correlation between urine CA125 and serum CA125 measurements. Ovarian cancer patients were found to have about 4-5 fold higher level of CA125 activity in urine compared to normal women or women with benign ovarian tumors.

All references cited herein are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

What is claimed is:

1. A method of diagnostically evaluating a woman for ovarian cancer, said method comprising:
   (a) obtaining a test urine sample from said woman;
   (b) assaying said test urine sample to determine the amount or concentration of at least one CA125 peptide selected from the group consisting of:
      (1) a CA125 peptide consisting of the amino acid sequence of SEQ ID NO: 1;
      (2) a CA125 peptide consisting of the amino acid sequence of SEQ ID NO: 2;
      (3) a CA125 peptide consisting of the amino acid sequence of SEQ ID NO: 3;
   (c) comparing the results obtained from the assay of step (b) with results from an assay of one or more control urine samples acquired from women not afflicted with ovarian cancer; and
   (d) concluding that said woman is positive for ovarian cancer if the amount or concentration of said at least one CA125 peptide is higher in said test urine sample than in said one or more control urine samples.

2. The method of claim 1, wherein the amount or concentration of said CA125 peptide in said test urine sample is at least 3 times higher than in said one or more control urine sample.

3. The method of claim 2, wherein the assays of said test urine sample and said one or more control urine sample comprise a radioimmunoassay (RIA), an Enzyme Linked Immunosorbent Assay (ELISA), a chromatographic assay or mass spectroscopy.

4. The method of claim 1, further comprising assaying the plasma or serum of said woman for CA125.

5. The method of claim 1, wherein said woman has not been previously diagnosed as having ovarian cancer and said method is used to evaluate whether ovarian cancer is present.

6. The method of claim 1, wherein said woman has been diagnosed as having ovarian cancer and said method is used to determine if said ovarian cancer has recurred or advanced.

7. The method of claim 1, wherein said method comprises detecting a CA125 peptide consisting of the amino acid sequence of SEQ ID NO: 1.

8. The method of claim 1, wherein said method comprises detecting a CA125 peptide consisting of the amino acid sequence of SEQ ID NO: 2.

9. The method of claim 1, wherein said method comprises detecting a CA125 peptide consisting of the amino acid sequence of SEQ ID NO: 3.

10. The method of claim 7, wherein the amount or concentration of said CA125 peptide consisting of the amino acid sequence of SEQ ID NO:1 in said test urine sample is at least 3 times higher than in said one or more control urine samples.

11. The method of claim 10, wherein the assays of said test urine sample and said one or more control urine samples comprise a radioimmunoassay (RIA), an Enzyme Linked Immunosorbent Assay (ELISA), a chromatographic assay or mass spectroscopic assay.

12. The method of claim 11, further comprising assaying the plasma or serum of said woman for CA125.

13. The method of claim 11, wherein said woman has been diagnosed as having ovarian cancer and said method is used to determine if said ovarian cancer has recurred or advanced.

14. The method of claim 8, wherein the amount or concentration of said CA125 peptide consisting of the amino acid sequence of SEQ ID NO:2 in said test urine sample is at least 3 times higher than in said one or more control urine samples.

15. The method of claim 14, wherein the assays of said test urine sample and said one or more control urine samples comprise a radioimmunoassay (RIA), an Enzyme Linked Immunosorbent Assay (ELISA), a chromatographic assay or mass spectroscopic assay.

16. The method of claim 15, further comprising assaying the plasma or serum of said woman for CA125.

17. The method of claim 15, wherein said woman has been diagnosed as having ovarian cancer and said method is used to determine if said ovarian cancer has recurred or advanced.

18. The method of claim 9, wherein the amount or concentration of said CA125 peptide consisting of the amino acid sequence of SEQ ID NO:3 in said test urine sample is at least 3 times higher than in said one or more control urine samples and wherein the assays of said test urine sample and said one or more control urine samples comprise a radioimmunoassay (RIA), an Enzyme Linked Immunosorbent Assay (ELISA), a chromatographic assay or mass spectroscopic assay.

19. The method of claim 18, further comprising assaying the plasma or serum of said woman for CA125.

20. The method of claim 18, wherein said woman has been diagnosed as having ovarian cancer and said method is used to determine if said ovarian cancer has recurred or advanced.

* * * * *